United States Patent
Assmann et al.

Patent Number: 5,514,820
Date of Patent: May 7, 1996

[54] CONTINUOUS PROCESS FOR THE PRODUCTION OF LOWER ALKYL ESTERS

[75] Inventors: Georg Assmann, Juechen; Gerhard Blasey, Duesseldorf; Bernhard Gutsche, Hilden; Lutz Jeromin, Hilden, all of Germany; Jean Rigal; René Armengaud, both of Saint-Martory; Bernard Cormary, Salies du Salat, all of France

[73] Assignee: Henkel Kommanditgesellschaft auf Aktien, Duesseldorf, Germany

[21] Appl. No.: 191,746

[22] Filed: Feb. 3, 1994

Related U.S. Application Data

[63] Continuation of Ser. No. 844,625, Jun. 1, 1992, abandoned.

[30] Foreign Application Priority Data

Sep. 29, 1989 [DE] Germany .......................... 39 32 514.8

[51] Int. Cl.⁶ ..................................................... C11C 3/04
[52] U.S. Cl. .................................................... 554/167
[58] Field of Search ...................................... 554/167

[56] References Cited

U.S. PATENT DOCUMENTS 2,360,844  11/1941  Bradshaw et al. ................ 260/410.9

FOREIGN PATENT DOCUMENTS

| 0131991 | 1/1985 | European Pat. Off. . |
| 3020612 | 12/1980 | Germany . |
| 634411 | 3/1950 | United Kingdom . |

OTHER PUBLICATIONS

Seifen, Öle, Fette, Wachse, Modern Production Technology for Fatty Acid Methylester—Derived Surfactants and Soap, 1988, pp. 595–600.

*Primary Examiner*—José G. Dees
*Assistant Examiner*—Deborah D. Carr
*Attorney, Agent, or Firm*—Ernest G. Szoke; Wayne C. Jaeschke; Henry E. Millson, Jr.

[57] ABSTRACT

The invention relates to a continuous process for the production of lower alkyl esters at temperatures of up to 100° C. and under pressures of up to 10 bar by reaction of fatty acid triglycerides containing less than 1% free fatty acid with a lower alcohol in two stages in the presence of a homogeneous alkaline catalyst, the glycerol formed being removed after the first stage. To enable the process to be carried out with high yields and with lower maintenance, investment and energy costs than in the prior art, the reaction mixture is passed through a reactor and a following static separator only once in each stage, tube reactors are used as the reactors and the Reynolds number of the flow of the reaction mixture is greater than 2,300.

13 Claims, 1 Drawing Sheet

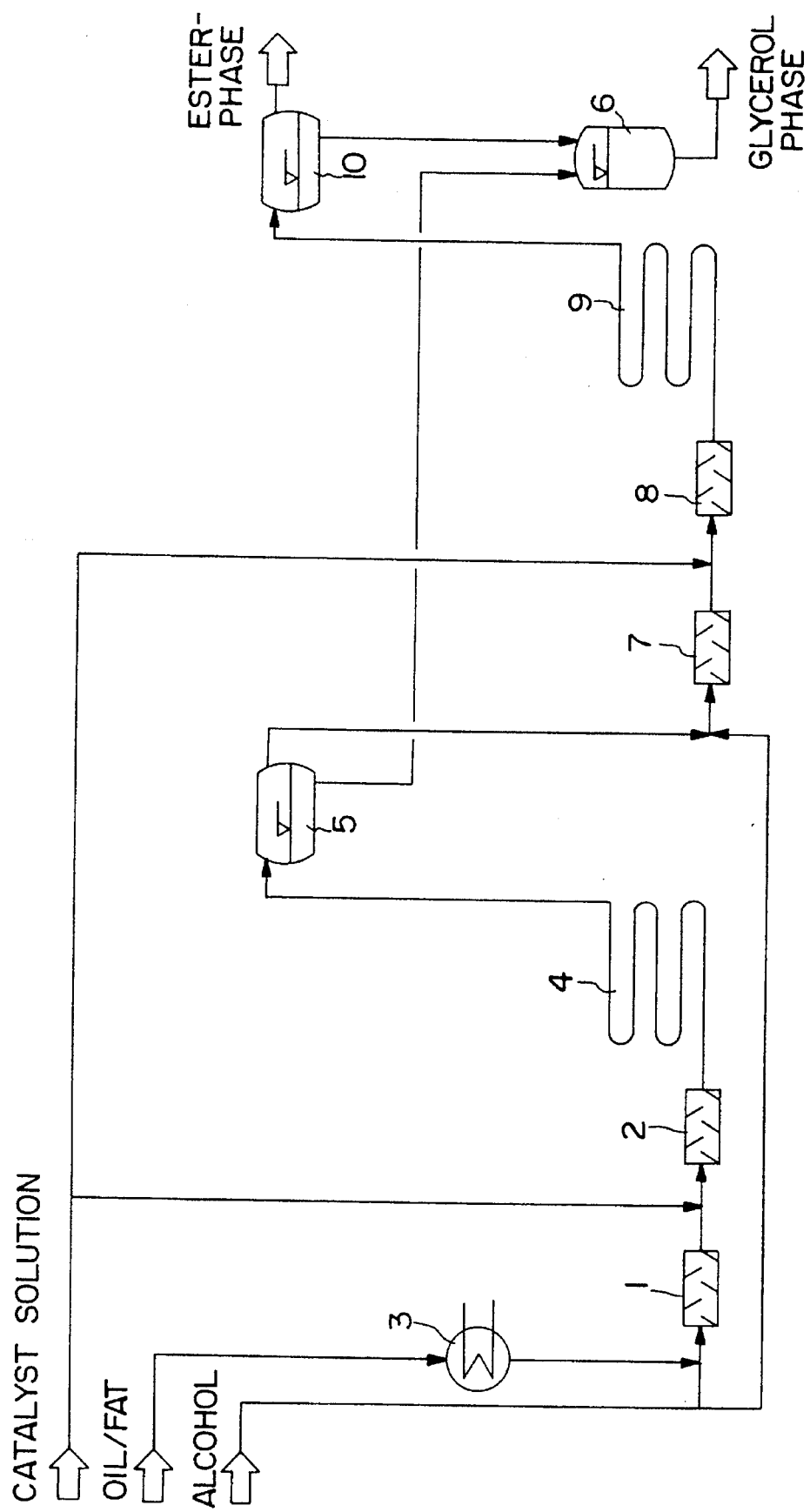
FIG. I

CONTINUOUS PROCESS FOR THE PRODUCTION OF LOWER ALKYL ESTERS

This application is a continuation of application Ser. No. 07/844,625 filed on Jun. 1, 1992, now abandoned.

This invention relates to a continuous process for the production of lower alkyl esters, more particularly methyl esters, at temperatures of up to 100° C. and under pressures of up to 10 bar by reaction of fatty acid triglycerides containing less than 1% free fatty acid (ffa) with a lower alcohol, more particularly methanol, in at least two stages in the presence of a homogeneous alkaline catalyst, the glycerol formed being removed from the reaction mixture after each stage.

The production of alkyl esters and glycerol from natural fats and oils is a chemical process which has been practised for decades. The two processes mainly used are high-pressure transesterification under pressures of up to 90 bar and at temperatures of up to 250° C. and low-pressure transesterification under pressures of 1 to 10 bar and at temperatures below 100° C.

Deacidified oils and fats with a low percentage content of free fatty acids are used in low-pressure transesterification. Where an alkaline catalyst is used, the catalyst is neutralized by the free fatty acid, so that its activity is no longer available. The alkaline catalysts used include sodium methylate, sodium hydroxide, potassium hydroxide and others. Other catalysts are mentioned in the Article in J. Scient. Ind. Res. Vol. 33, April 1974, pages 178–187.

In the most simple form of the process, namely low-pressure transesterification, the mixture prepared is reacted for a few minutes to several hours in a stirred tank. The light phase, namely the alkyl ester, and the glycerol phase are then decanted in the same tank. A brief description can be found in GB-PS 6,344,411 and in U.S. Pat. No. 2,360,844.

The disadvantage of this simple procedure lies in the high consumption of alcohol and alkaline catalyst required in the transesterification reaction to obtain a high conversion because the transesterification is an equilibrium reaction. The large excess of catalyst and alcohol complicates the decantation of glycerol with alcohol on the one hand and the actual recovery of glycerol thereafter on the other hand. This is because, in the recovery of glycerol, the soaps formed from the catalyst have to be broken down by inorganic acid with addition of water. The fatty acids may then be separated from the crude glycerol by decantation.

To obtain a sufficiently high yield despite the use of relatively small quantities of alcohol and alkaline catalysts, the transesterification has to be carried out in two stages. Thus, in the discontinuous low-pressure transesterification carried out in a stirred tank in accordance with DE-PS 3 020 612, the glycerol present as the phase is removed from the reaction mixture after a first reaction stage and subsequent decantation while the upper phase is again transesterified. For the removal of glycerol, water is added after the second stage to improve separation. Although this results in the effective removal of glycerol, it does involve additional effort when it comes to working up the glycerol.

An improved low-pressure transesterification process is described in an Article in Seifen, Öle, Fette, Wachse, 1988, pages 595 to 600, cf. in particular FIG. 3 on page 596 and the associated description. The process in question is a continuous two-stage process. The starting materials low-ffa oil, methanol and alkaline catalyst are introduced by a pump into a first reaction loop. The reaction mixture is transported by a centrifugal pump into a first reactor. The centrifugal pump performs the additional function of thoroughly mixing the reaction mixture. After the appropriate residence time in the reactor, the mixture flows into a static vertical separator. After decantation, the upper phase is returned to the centrifugal pump while the lower phase, which contains almost all the glycerol formed together with residual methyl ester and unreacted triglycerides, is delivered to a centrifuge for better separation of the glycerol. The upper phase freed from the glycerol then passes through a second reaction loop. Each reaction loop consists of a centrifugal pump, a reactor and a static separator. The pump in each reaction loop is necessary because the reacted mixture is recycled in each loop. Since separation in the static separator is incomplete in this known process, the centrifuge mentioned is necessary for the separation of glycerol.

The problem addressed by the present invention was to provide a continuous process of the above-mentioned type for the production of lower alkyl esters in high yields which would require lower maintenance, capital investment and energy costs and which would be simple and safe to operate.

According to the invention, this problem is solved by the fact that the reaction is carried out in at least two stages in a tube reactor. The reaction mixture passes through the tube reactor and the following horizontal static separator only once in each stage. Thorough mixing by turbulence must be present in the tube reactors, the Reynolds number $$Re = \frac{\zeta v d}{\eta}$$

in which $\zeta$ is the density of the mixture, v is the average tube velocity, d is the internal tube diameter and $\eta$ is the viscosity of the mixture, being used as the characteristic value in this regard. The Re number is calculated for the entrance of the first tube reactor.

The turbulence must be present in any event. The turbulence range begins beyond a Reynolds number of 2,300. For many applications, a Reynolds number of greater than 4,000 is preferred. Very safe operation was observed with a Reynolds number of 10,000. A Reynolds number of greater than 10,000 is even more preferred.

In the calculation of the Reynolds number, density is calculated in accordance with the known relation at the reaction temperature. The relation is used for the average density of a pseudo-monophase mixture:

$$\frac{1}{\zeta} = \sum_i \frac{w_i}{i}$$

where $\zeta$ is the density of component i in kg/m$^3$ and $w_i$ is the mass content of that component.

Alternatively, density may even be determined with a densimeter. A corresponding relation applies in the case of viscosity. In addition to the experimental determination of $\eta$ using a viscosimeter, the pseudo mixture viscosity may be calculated in accordance with the following equation:

$$\ln \eta = \sum_i x_i \ln \eta_i$$

where $\eta_i$ is the viscosity of component i in kg/ms and $x_i$ is the mole fraction of component i.

The tube length is obtained from investigations of the reaction kinetics from which the residence time for a given conversion may be derived. Since the velocity in the tube is predetermined, the tube length is calculated from the required residence time. The residence time in the tube is between 1 and 10 minutes, a residence time of about 2 to 5 minutes being advantageous in the production of methyl ester. The limiting factor for the length of the tube reactor can be the pressure loss in the tube. In the production of alkyl esters from oils and fats using sodium methylate as catalyst, only a slight pressure loss of less than 1 bar for pressures of 2 to 10 bar was observed.

Besides thorough mixing of the starting materials, it is particularly important to the transesterification reaction that no glycerol (reaction product) come into contact with starting oil, methanol and new catalyst (back-mixing) because, if this were the case, the glycerol would partly back-react with the ester to form the mono-, di- and triglyceride. These glycerides would have to be degraded again which would involve increased effort with a relative deterioration in the conversion. Accordingly, a residence time distribution corresponding to that in the tube reactor is required. It is known from the laboratory tests using a continuously operated stirred tank that, for the same excess of alcohol and the same concentration of catalyst, the transesterification reaction for coconut oil takes approximately 15 minutes to reach the conversion obtained after a residence time of 2 minutes in a corresponding tube reactor.

In one advantageous embodiment, the two liquid phases are separated in horizontal tubular separators. The reaction mixture flows into the separator at one end and the upper phase and lower phase (glycerol) flow off separately at the opposite end. In this case, the after-reaction takes place when the reaction mixture begins to flow in, separation taking place at the same time. The after-reaction and separation are terminated towards the end of the separator. Since the separator is a tubular separator, there is no back-mixing of ester already separated with ester to be after-reacted. In continuously operated vertical separators in the form of stirred tanks, this gradual transition from after-reaction and separation would not be possible without the removal of glycerol phase in the ester. Through the after reaction, the yield of methyl ester is increased by up to 20%.

In another embodiment of the invention, the residence time of the reaction mixture in the separators is 0.1 to 5 hours and the reaction mixture is kept at the reaction temperature in the separators.

In the production of methyl ester, the separation time should be between 15 minutes and 2 hours.

The alkyl ester obtained still contains residues of alcohol and catalyst. In the second stage, which is laid out according to the same aspects as the first stage, alcohol and catalyst are additionally introduced. After mixing and decantation, triglyceride conversions totalling 98% are obtained.

A further saving of alcohol and catalyst is achieved by carrying out the process in three stages. The additional outlay on equipment is of particular advantage for transesterifications involving higher alcohols, ethanol, butanol, etc.), where a glycerol phase can even be separated at low conversions, and affords further advantages in the production of the corresponding alkyl esters. At the same time, the excess of alcohol and the quantity of catalyst required can be further reduced.

Providing a high conversion is maintained, the alcohol input can be reduced by comparison with known processes if the starting alcohol-to-triglyceride ratio in both stages is from 4.5 to 7.5 mol/mol triglyceride and, particularly in the production of methyl ester, from 5.1 to 6.9 mol/mol triglyceride.

If the high conversion is maintained, the input of catalyst and alcohol is kept low in this new process: the total concentration of catalyst (for example sodium methylate) in both stages taken together is less than 0.25% by weight, based on neutral triglyceride, and the total quantity of alcohol and catalyst to be used is divided between both stages, depending on the quality and chain length distribution of the triglyceride to be transesterified, in such a way that a conversion of at least 85% is obtained in each stage. The catalyst input in the second stage can be kept at ≦0.05%.

For preliminary mixing, the reaction mixture may be passed through static mixers.

EXAMPLES

1. Transesterification of Rapeseed Oil

In a pilot plant, deacidified rapeseed oil (approx. 150 l/h) is introduced into a tube reactor at 75° C./3 bar. Methanol and sodium methylate are added in the form of a solution at 20° C. The ratio of methanol to oil was 0.2 for the first stage and 0.04 for the second stage. The catalyst was introduced in quantities of 0.2% and 0.04% by weight, based on neutral oil. For a residence time of 2 minutes, the conversion amounted to 90%. After the separation of glycerol over a period of 2 hours, a total conversion of 98% was obtained after the second stage. The adjusted Re number was 2,700 (entrance of first reactor).

2. Transesterification of Coconut Oil

In a two-stage transesterification plant with tube reactors and intermediate separation, 5,000 l/h coconut oil were transesterified with flaked sodium hydroxide methanol, the catalyst having been dissolved in methanol. The ratio of methanol to oil was 0.3 in the first stage and 0.04 in the second stage. The ratio of catalyst to neutral oil was adjusted to 0.24% in the first stage and to 0.04% in the second stage. A conversion of 88% was obtained after the first stage, so that the total conversion after the second stage was 98%. The Re number at the entrance to the first reactor was 7,500.

BRIEF DESCRIPTION OF DRAWINGS

An example of an embodiment of the invention is described in more detail in the following with reference to FIG. 1 of the accompanying drawing.

FIG. 1 shows the construction of a plant for operating the process according to the invention. Oil, methanol and catalyst solution are delivered from storage tanks into the first reaction section through two static mixers (1 and 2). The natural oil, i.e. triglyceride, is heated in the heat exchanger (3) and mixed intensively with cold methanol in the first static mixer (1). The catalyst is then added, so that the reaction can take place in the tube reactor (4). The reaction mixture then enters the first horizontal static separator (5), in which it after-reacts, and is separated into two phases in the separator towards the end of the residence time. The lower phase is delivered to a glycerol receiver (6); the upper phase passes through another stage with a static mixer (7 and 8), a second tube reactor (9) and a second horizontal separator (10). Methanol and catalyst solution are introduced into the second stage (7 and 10) in the same way as into the first stage. The lower phase of the second static separator is also delivered to the glycerol receiver (6), after which the glycerol phase is further purified. The upper phase is recovered as the methyl ester phase.

| List of reference numerals | |
| --- | --- |
| 1, 2, 8, 9 | static mixers |
| 3 | heat exchanger |
| 4, 9 | tube reactors |
| 5, 10 | static separators |

| List of reference numerals | |
| --- | --- |
| 6 | glycerol receiver |

We claim:

1. In a process for the manufacture of lower alkyl esters by the reaction of fatty acid triglycerides containing less than 1% free fatty acid with a lower alcohol at a temperature up to 100° C. and at a pressure up to 10 bar in the presence of a homogeneous alkaline catalyst, the improvement wherein the reaction mixture is passed through at least two stages in which in each stage the reaction mixture is passed through a single horizontally oriented tubular reactor and a following static separator in which glycerol is removed from the reaction mixture, and wherein the Reynolds number of the flow of the reaction mixture at the entrance of the first tubular reactor is greater than 2,300, the Reynolds number being calculated from the formula $$Re = \frac{\zeta v d}{\eta}$$

in which Re is the Reynolds number, $\zeta$ is the density of the mixture, v is the average tube velocity, d is the internal tube diameter and $\eta$ is the viscosity of the mixture.

2. The process of claim 1 wherein the Reynolds number is greater than 4,000.

3. The process of claim 1 wherein the Reynolds number is greater than 10,000.

4. The process of claim 1 wherein the residence time of the reaction mixture in the static separators is from 0.1 to 5 hours and wherein the reaction mixture is kept at the reaction temperature in the static separators.

5. The process of claim 4 wherein the lower alcohol is methanol and the residence time of the reaction mixture in the static separators is from 1 to 2 hours.

6. The process of claim 1 wherein the static separators are tubular horizontal separators into one end of which the reactor mixture enters, then separates into an ester upper phase and a glycerol lower phase, and the two phases leave separately at the opposite end from which the reaction mixture enters.

7. The process of claim 1 wherein the residence time of the reaction mixture in each tubular reactor is from 1 to 10 minutes.

8. The process of claim 1 wherein the lower alcohol is methanol and the residence time of the reaction mixture in each tubular reactor is from 2 to 5 minutes.

9. The process of claim 1 wherein in each stage the lower alcohol and fatty acid triglycerides are present in a ratio of from 4.5 to 7.5 mols of alcohol per mole of triglycerides.

10. The process of claim 9 wherein the lower alcohol is methanol and said ratio is from 5.1 to 6.9 mols of methanol per mole of triglycerides.

11. The process of claim 1 wherein the total concentration of alkaline catalyst in the at least two stages is less than 0.25% by weight, based on the weight of neutral triglycerides, and wherein the total quantity of alkaline catalyst and lower alcohol used in the process is divided among the stages so that a conversion to lower alkyl ester of at least 85% is obtained in each stage.

12. The process of claim 1 wherein the reaction mixture used in the first stage is mixed prior to use in a static mixer.

13. The process of claim 1 wherein the lower alcohol is methanol; the Reynolds number is greater than 10,000; the residence time of the reaction mixture in each tubular reactor is from 2 to 5 minutes and the residence time of the reaction mixture in the static separators is from 1 to 2 hours; the static separators are tubular horizontal separators; and the ratio of methanol to triglycerides in each stage is from 5.1 to 6.9 moles of methanol per mole of triglycerides.

* * * * *